(12) United States Patent
Horwitz et al.

(10) Patent No.: US 7,470,788 B2
(45) Date of Patent: Dec. 30, 2008

(54) ANTITUMOR AGENTS

(75) Inventors: Jerome P. Horwitz, Farmington Hills, MI (US); Lisa Polin, Oak Park, MI (US); Stuart T. Hazeldine, Taylor, MI (US); Thomas H. Corbett, Grosse Pointe Park, MI (US)

(73) Assignee: Wayne State University, Detroit, MI (US)

( * ) Notice: Subject to any disclaimer, the term of this patent is extended or adjusted under 35 U.S.C. 154(b) by 202 days.

(21) Appl. No.: 11/223,806

(22) Filed: Sep. 9, 2005

(65) Prior Publication Data

US 2007/0060612 A1    Mar. 15, 2007

Related U.S. Application Data

(63) Continuation-in-part of application No. 11/220,894, filed on Sep. 7, 2005, now abandoned.

(51) Int. Cl.
*C07D 215/38* (2006.01)
(52) U.S. Cl. ...................................................... 546/157
(58) Field of Classification Search ................. 546/157; 514/312
See application file for complete search history.

(56) References Cited

U.S. PATENT DOCUMENTS

| | | | |
|---|---|---|---|
| 4,629,493 A | 12/1986 | Ura et al. | |
| 6,867,219 B2 * | 3/2005 | Horwitz et al. | 514/312 |
| 7,109,341 B2 * | 9/2006 | Horwitz et al. | 546/157 |
| 2007/0054938 A1 | 3/2007 | Horwitz et al. | |

FOREIGN PATENT DOCUMENTS

| | | |
|---|---|---|
| WO | WO-03/011832 A1 | 2/2003 |
| WO | WO-2004/005260 A1 | 1/2004 |
| WO | WO-2007/030780 A2 | 3/2007 |
| WO | WO-2007030780 A3 | 3/2007 |

OTHER PUBLICATIONS

Corbett, T. H., "Preclinical Antitumor Efficacy of Analogs of XK469: Sodium-(2-[4-(7-chloro-2-quinoxalinyloxy)phenoxy] Propionate", *Martinus Nijhoff Publishers, Investigational New Drugs*, 16, 2, (1998),129-139.

"Invitation to Pay Additional Fees and Partial International Search Report for corresponding PCT Application No. PCT/US2006/035184", (Mar. 22, 2007), 8 pgs.

Hazeldine, S. T., "Design, Synthesis, and Biological Evaluation of Analogues of the Antitumor Agent, 2-{4-[(7-Chloro-2-quinoxalinyl)oxy]phenoxy} propionic Acid (XK469)", *Journal of Medicinal Chemistry*, 44(11), (2001), 1758-1776.

"International Application No. PCT/US2006/035184 International Search Report and Written Opinion mailed Jul. 2, 2007", 20 pgs.

* cited by examiner

*Primary Examiner*—D. Margaret Seaman
(74) *Attorney, Agent, or Firm*—Schwegman, Lundberg & Woessner, P.A.

(57) ABSTRACT

The invention provides compounds of formula I:

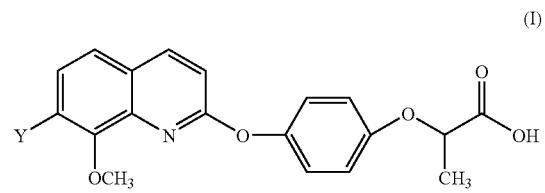

(I)

wherein Y is F, Cl or Br; or a pharmaceutically acceptable salt thereof. The compounds are effective antitumor agents. The invention also provides pharmaceutical compositions comprising a compound of formula I or a salt thereof, intermediates useful for preparing a compound of formula I, and therapeutic methods comprising administering a compound of formula I or a salt thereof to a mammal in need thereof.

16 Claims, No Drawings

ANTITUMOR AGENTS

PRIORITY OF INVENTION

This application is a continuation-in-part (CIP) application of U.S. application Ser. No. 11/220,894 titled Antitumor Agents, filed on Sep. 7, 2005 now abandoned.

GOVERNMENT FUNDING

The invention described herein was made in part with government support under NCI-NIH Grant Number CA82341 awarded by the National Cancer Institute. The United States Government has certain rights in the invention.

BACKGROUND OF THE INVENTION

U.S. Pat. No. 4,629,493 discloses herbicidal compounds of the following formula:

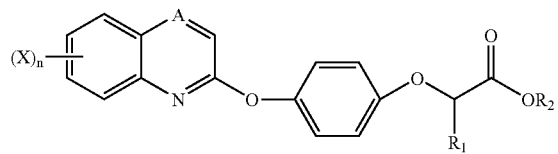

wherein A is —CH— or —N—; X is a halogen; n is 0, 1, or 2; $R^1$ is hydrogen or a lower alkyl group; and $R^2$ is —OH, among other values. One of these compounds is currently sold commercially for the control of annual and perennial grass weeds in broadleaf crops. This compound has the following formula:

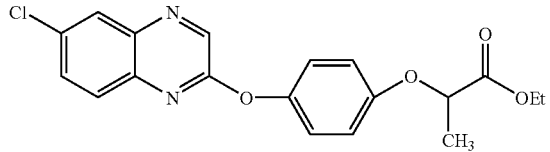

Corbett et. al., *Investigational New Drugs*, 16 129-139 (1998) evaluated a series of quinoxaline compounds for activity against solid tumors in mice. The following compound (referred to as XK469) was reported to have broad activity against transplantable mouse tumors.

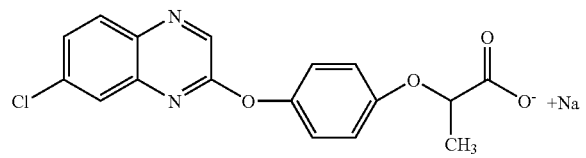

The compound was also reported to have a relatively low potency, and to produce several undesirable side effects, including in vivo toxicity, e.g., paralytic ileus, GI-epithelial damage, marrow toxicity, neuromuscular toxicity and weight loss.

U.S. Pat. No. 6,867,219 claims and discloses compounds of the formula:

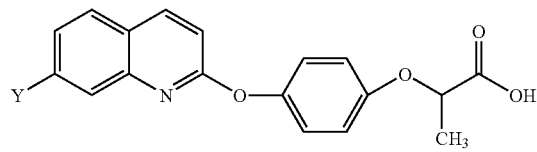

wherein Y is F, Cl, Br, methyl or methoxy; or a pharmaceutically acceptable salt thereof. These compounds are reported to have antitumor activity.

There is currently a need for additional antitumor agents.

SUMMARY OF THE INVENTION

The present invention provides compounds that are effective antitumor agents. Accordingly, there is provided a compound of the invention which is a compound of formula I:

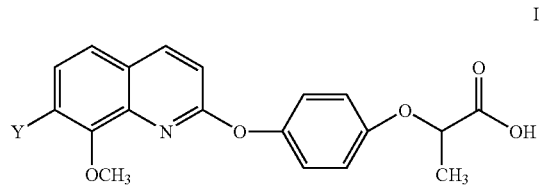

wherein Y is F, Cl or Br; or a pharmaceutically acceptable salt thereof.

The invention also provides a therapeutic method to inhibit tumor cell growth in a mammal, comprising administering to a mammal in need of such therapy, an effective amount of a compound of the invention.

The invention also provides a therapeutic method to treat cancer in a mammal, comprising administering to a mammal in need of such therapy, an effective amount of a compound of the invention.

The invention also provides the use of a compound of the invention in medical therapy.

The invention also provides the use of a compound of the invention to manufacture a medicament for the treatment of cancer in a mammal.

DETAILED DESCRIPTION OF THE INVENTION

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine antitumor activity using the standard tests described herein, or using other similar tests which are well known in the art.

A specific value for Y is F.

Another specific value for Y is Cl.

A specific value for Y is Br.

A specific groups of compounds of Formula (I) are compounds wherein the carbon bearing the methyl group is the (R) configuration.

Another specific groups of compounds of Formula (I) are compounds wherein the carbon bearing the methyl group is the (S) configuration.

Preferred compounds of the invention include 2-(4-(7-fluoro-8-methoxyquinolin-2-yloxy)phenoxy)propanoic acid; 2-(4-(7-chloro-8-methoxyquinolin-2-yloxy)propanoic acid; 2-(4-(7-bromo-8-methoxyquinolin-2-yloxy)phenoxy)propanoic acid; and pharmaceutically acceptable salts thereof.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example, calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thiomersal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, dimethyl sulfoxide (DMSO), alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820, 508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The compound is conveniently administered in unit dosage form; for example, containing 5 to 1000 mg/m$^2$, conveniently 10 to 750 mg/m$^2$, most conveniently, 50 to 500 mg/m$^2$ of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compounds of the invention are effective anti-tumor agents and have higher potency and/or reduced toxicity as compared to XK 469. Preferably, compounds of the invention are more potent and less toxic than (R) XK 469, and/or avoid a potential site of catabolic metabolism encountered with XK469, i.e., have a different metabolic profile than XK469.

The present invention provides therapeutic methods of treating cancer in a mammal, which involve administering to a mammal having cancer an effective amount of a compound or a composition of the invention. A mammal includes a primate, human, rodent, canine, feline, bovine, ovine, equine, swine, caprine, bovine and the like. Cancer refers to any various type of malignant neoplasm, for example, colon cancer, breast cancer, melanoma and leukemia, and in general is characterized by an undesirable cellular proliferation, e.g., unregulated growth, lack of differentiation, local tissue invasion, and metastasis.

The ability of a compound of the invention to treat cancer may be determined by using assays well known to the art. For example, the design of treatment protocols, toxicity evaluation, data analysis, quantification of tumor cell kill, and the biological significance of the use of transplantable tumors screens are documented. In addition, ability of a compound to treat cancer may be determined using the Tests as described below.

In Experiment # 2877A the following general methodologies were employed:

Tumor and Animal Maintenance

Mammary adenocarcinoma-16/C were used in the studies. Tumors were maintained in the mouse strain of origin $C_3H$ (for the mammary tumors). Individual mouse body weights for each experiment were within 5 grams, and all mice were over 17 grams at the start of therapy. The mice were supplied food and water ad libitum.

Chemotherapy of Solid Tumors

Animals were pooled, implanted subcutaneously with 30 to 60 mg tumor fragments by a 12 gauge trocar on day 0, and again pooled before unselective distribution to the various treatment and control groups. For early stage treatment, chemotherapy was started within 1 to 3 days after tumor implantation while the number of cells was relatively small ($10^7$ to $10^8$ cells). Tumors were measured with a caliper twice weekly. Mice were sacrificed when their tumors reached 1500 mg. Tumor weights are estimated from two-dimensional measurements:

Tumor weight (in mg)=$(a \times b^2)/2$, where a and b are the tumor length and width in (mm), respectively.

End Points for Assessing Antitumor Activity for Solid Tumors

The following quantitative endpoints were used to assess antitumor activity:

a) Tumor growth delay (T–C value), where T is the median time (in days) required for the treatment group tumors to reach a predetermined size (e.g., 1000 mg), and C is the median time (in days) for the control group tumors to reach the same size. Tumor-free survivors were are excluded from these calculations (cures are tabulated separately). This value is an important criterion of antitumor effectiveness because it allows the quantification of tumor cell kill.

b) Calculation of tumor cell kill For subcutaneously (SC) growing tumors, the $\log_{10}$ cell kill was calculated from the following formula:

$$\text{The } \log_{10} \text{ cell kill total (gross)} = \frac{T-C \text{ value in days}}{(3.32)(Td)}$$

where T–C is the tumor growth delay as described above and Td is the tumor volume doubling time (in days), estimated from the best fit straight line from a log-linear growth plot of the control group tumors in exponential growth (100 to 800 mg range). The conversion of the T–C values to $\log_{10}$ cell kill is possible because the Td of tumors regrowing post treatment (Rx) approximates the Td values of the tumors in untreated control mice.

The issue of conversion of tumor growth delay (T–C value) to log tumor cell kill is justified in this series because of the large number of cures obtained with 5 of the agents in this XK469 series that have been previously studied and patented. Cures are a clear indication of tumor cell kill (rather than stasis of tumor cell replication).

In selected cases, both for historic in vivo evaluation data as well as data presented here, it is of value to compare log kill numbers from trials of markedly different testing schedules. For this purpose, an activity table was created, and is presented below. It should be noted that an activity rating of +++ to ++++ is needed to effect partial regression (PR) or complete regression (CR) of 100 to 300 mg size masses of most transplanted solid tumors of mice. Thus, an activity rating of + or ++ would not be scored as active by usual clinical criteria. A PR is a reduction in tumor mass to less than 50% of pretreatment size. A CR is a reduction in tumor mass to below palpable size (i.e., reduction to zero detectable mass).

| Conversion of $\log_{10}$ tumor cell kill to an activity rating | | |
|---|---|---|
| Antitumor activity | | Duration of Rx 5 to 20 days $\log_{10}$ kill (gross) |
| Highly active | ++++ | >2.8 |
| | +++ | 2.0-2.8 |
| | ++ | 1.3-1.9 |
| | + | 0.7-1.2 |
| | − | <0.7 |

The treatment and control groups were measured when the control group tumors reach approximately 700 to 1200 mg in size (median of group). The T/C value in percent is an indication of antitumor effectiveness: A T/C=0% means no tumor growth. A T/C=100% means no antitumor activity, i.e., the treated and control tumors grew equally. A T/C equal to or less than 42% is considered significant antitumor activity by the Drug Evaluation Branch of the Division of Cancer Treatment (NCI). A T/C value<10% is considered to indicate highly significant antitumor activity, and is the level used by NCI to justify a clinical trial if toxicity, formulation, and certain other requirements are met (termed DN-2 level activity). A body weight loss nadir (mean of group) of greater than 20% or greater than 20% drug deaths is considered to indicate an excessively toxic dosage in most single course trials.

The invention will now be illustrated by the following non-limiting examples:

EXAMPLE 1

Synthesis of (R)-2-(4-(7-halo-8-methoxyquinolin-2-yloxy)phenoxy)propanoic acid

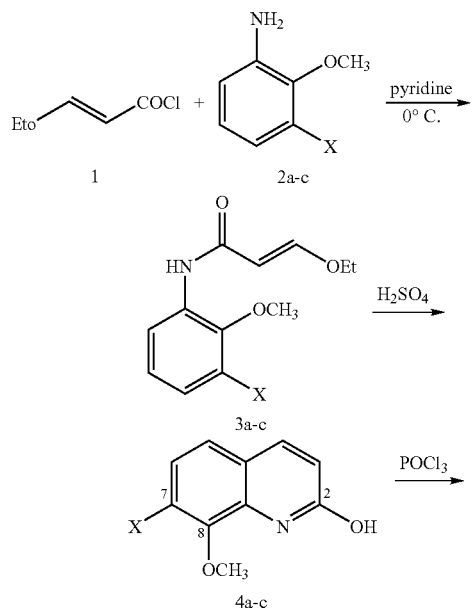

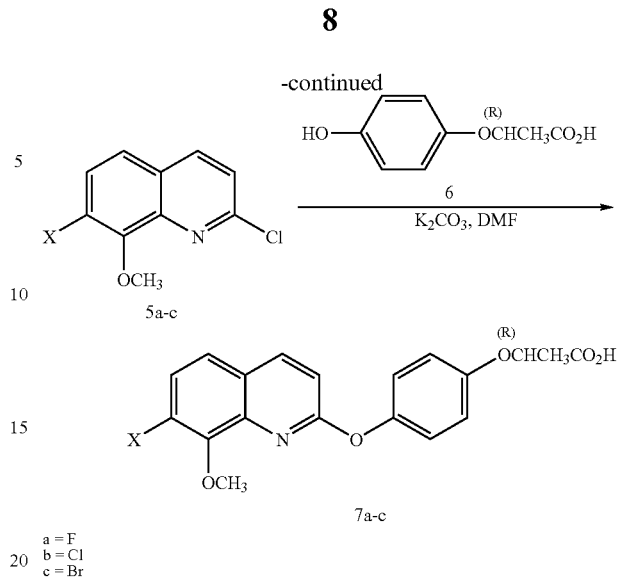

a = F
b = Cl
c = Br (E)-3-Ethoxy-N-(3-fluoro-2-methoxyphenyl)acrylamide (3a)

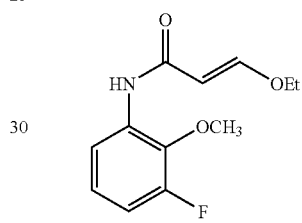

A mixture of 6-fluoro-o-anisidine (2a) (5.08 g, 36 mmol), DMAP (0.44 g, 3.6 mmol) and pyridine (25 mL) was stirred in an ice bath for one hour. After concentrating, water (50 mL) and AcOEt (100 mL ) were added. Concentrated HCl was added to pH 1. Extraction was performed with AcOEt as the organic layer was washed with was washed successively with: 25 mL saturated NaCl containing 2 mL 1 M HCl, 25 mL saturated NaCl containing 5 mL NaHCO$_3$, and finally with 25 mL saturated NaCl. The organic layer was dried with MgSO$_4$ and purified by passing through a column of silica gel using a solvent system of 1:1 followed by 2:1 hexanes-AcOEt. The product was further purified by column chromatography using a solvent system combination of 10:1 4:1 2:1. The product was recrystalized from cold 10:1 hexanes-AcOEt to give (3.16 g, 37% yield) as off white crystals. $^1$H NMR (400 MHz, CDCl$_3$) 8.19 (d, J=8.4 Hz, 1H), 7.64 (d, J=11.2 Hz, 1H), 7.56 (bs, 1H), 7.01-6.94 (m, 1H), 6.81-6.74 (m, 1H), 5.36 (d, J=12 Hz, 1H), 3.98 (d, J=1.6 Hz, 3H), 3.96 (q, J=7.2 Hz, 2H), 1.36 (t, J=7.2 Hz, 3H). $^{19}$F NMR (376 MHz, CHCl$_3$) −131.37.

7-Fluoro-8-methoxyquinolin-2-ol (4a)

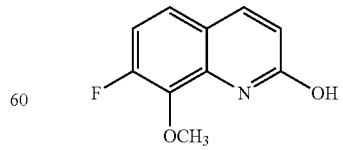

A mixture of (E)-N-(3-fluoro-2-methoxyphenyl)-3-ethoxypropenamide (3a) (3.16 g, 13.2 mmol) and 25 mL of concentrated H$_2$SO$_4$ was allowed to stir overnight at room temperature. The solution was poured over ice and concentrated NH$_3$ was added until pH 5 to precipitate out the product. The mixture was filtered, washed and dried to give the product (2.55 g, 87% yield) as a white solid. $^1$H NMR (400 MHz, DMSO-d6) 11.35 (bs, 1H), 7.86 (d, J=9.6Hz, 1H), 7.41 (dd, J=8.8, 5.6 Hz, 1H), 7.08 (dd, J=11.2, 8.8 Hz, 1H), 6.45 (d, J=10 Hz, 1H), 3.87 (s, 3H). $^{19}$F NMR (376 MHz, DMSO-d6) −128.88 (dd, J=11.5, 5.5 Hz).

2-Chloro-7-fluoro-8-methoxyquinoline (5a)

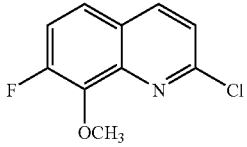

A mixture of 7-fluoro-8-methoxy-2-quinolinol (4a) (2.26 g, 11.7 mmol) and POCl$_3$ (5.5 mL, 60 mmol) was refluxed for 1.5 hours. The contents were concentrated and neutralized with NaHCO$_3$ and the mixture heated with water and AcOEt. The solution was filtered to remove undissolved impurities, followed by extraction. The organic layer was washed with saturated NaCl and dried with MgSO$_4$. The product was recrystalized from ***CHCl$_3$-hexanes, which yielded white crystals (2.24 g, 90% yield): mp 85-86° C.; $^1$H NMR (400 MHz, CDCl$_3$) 8.06 (d, J=8.8Hz, 1H) 7.48 (dd, J=8.8, 5.6 Hz, 1H), 7.37 (d, J=8.8 Hz, 1H), 7.35 (dd, J=9.2, 2.4 Hz, 1H), 4.23 (d, J=2.4 Hz, 3H). $^{19}$F NMR (376 MHz, CHCl$_3$) −127.35 (dd, J=10.9, 2.6 Hz).

2-(4-(7-Fluoro-8-methoxyquinolin-2-yloxy)phenoxy)propanoic acid (SH144)

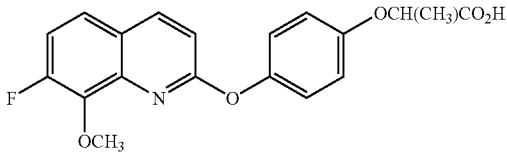

A mixture of 2-chloro-7-fluoro-8-methoxyquinoline (5a) (0.53 g, 2.5 mmol), 2-(4-hydroxyphenoxy) propionic acid (6a) (0.46 g, 2.5 mmol) and K$_2$CO$_3$ (0.86 g, 6.3 mmol) and DMF (5 mL) was heated for 21 h at 105° C. The mixture was concentrated to remove the DMF and the residue was dissolved in distilled water. The mixture was filtered through celite, chilled and acidified with 1 M HCl. The product was filtered, collected and dried. The product was dissolved in AcOEt and filtered through silica gel followed by column chromatography (1:1 hexanes-AcOEt). A more pure product (0.18 g, 20% yield) was obtained from recrystalization using CHCl$_3$-hexanes to give off white crystals: mp 143-145° C.; $^1$H NMR (400 MHz, CDCl$_3$) 9.63 (bs, 1H), 8.03 (d, J=9.2 Hz, 1H), 7.39 (dd, J=8.8, 4.8 Hz, 1H), 7.19 (dd, J=10.8, 9.2 Hz, 1H), 7.12-7.08 (m, 2H), 6.98-6.93 (m, 2H), 6.92 (d, J=8.8 Hz, 1H), 4.80 (q, J=7.2 Hz, 1H), 3.96 (s, 3H), 1.69 (d, J=6.4 Hz, 3H). $^{19}$F NMR (376 MHz, CDCl$_3$) −128.90 (m). $^{13}$C NMR (100 MHz, CDCl$_3$) 176.8, 162.4, 155.2 (J=247 Hz), 154.8, 148.0, 141.4 (m), 140.5, 128.4 (m), 123.5, 123.1, 122.6 (m), 116.4, 115.5 (J=23 Hz), 111.3, 73.0, 62.3, 18.7. IR (KBr) 3420 (OH), 1735 (C=O), 1615, 1495, 1470, 1435, 1330, 1260, 1235, 1200, 1135, 1085, 1045, 1005, 980, 945, 895, 875, 835, 815, 790, 715, 625, 605 cm−1. ESI-MS m/z 358 (M+1)+. Anal. (C19H16NFO5) C, 63.86; H, 4.51; N, 3.92. Found: C, 63.66; H, 4.41; N, 4.06. (R)-(+) enantiomer isolated as the sodium salt (off white crystals): mp 118 120° C.; [ ]D=30.8° (c=0.50, H2O). Chiral HPLC separation ((S) enantiomer, 6.9 min, (R) enantiomer, 8.0 min) using Astec Chirobiotic T, 250 mm 4.6 mm, 100 CH3OH: 0.1 AcOH: 0.1 TEA at 0.5 mL/min with detection at 236 nm.

(E)-N-(3-Chloro-2-methoxyphenyl)-3-ethoxyacrylamide (3b)

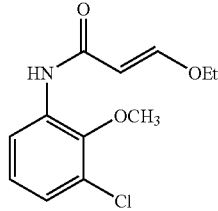

A mixture of 3-chloro o-anisidine (2b) (5.25 g, 33.3 mmoles) and pyridine (20 mL) were placed in an icebath. (E)-3-ethoxy-2-propenoyl chloride (1) (4 g, 40.1 mmol) was added dropwise as the solution stirred continuously for one hour. The mixture was concentrated to remove the pyridine and was transferred to a seperatory funnel where AcOEt and water were added. Concentrated HCl was added until the aqueous layer was pH 1. The water layer was extracted twice with AcOEt and the organic layers were washed with saturated NaCl (25 mL) containing 1 M HCl (2 mL). The procedure was followed by a second wash of saturated NaCl (25 mL) containing saturated NaHCO$_3$ (5 mL). The organic layer was finally washed with saturated 25 mL NaCl. The product layer was dried and filtered through silica gel (2 ) using a solvent system of 1:1 followed by 2:1 hexanes-AcOEt. The product was chromatographed (2:1 1:1 hexanes:AcOEt) and recrystalized from 10:1 hexanes-AcOEt to afford the product as off white crystals (4.19 g, 49% yield): mp 98-99° C.; $^1$H NMR (400 MHz, CDCl$_3$) 8.31 (dd, J=7.2, 2.4 Hz, 1H), 7.65 (d, J=12.4 Hz, 1H), 7.55 (bs, 1H), 7.07-7.04 (m, 2H), 5.36 (d, J=11.2 Hz, 1H), 3.97 (q, J=7.2 Hz, 2H), 3.89 (s, 3H), 1.37 (t, J=7.2 Hz, 3H).

7-Chloro-8-methoxyquinolin-2-ol (4b)

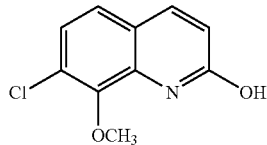

To conc H$_2$SO$_4$ (30 mL) was added to (E)-N-(3-chloro-2-methoxyphenyl)-3-ethoxypropenamide (3b) (3.73 g, 14.6 mmol) and allowed to stir overnight. The solution was poured over ice, filtered, washed and dried to give a yellow solid (2.85 g, 93% yield): $^1$H NMR (400 MHz, DMSO-d6) 11.45 (bs, 1H), 7.89 (d, J=10 Hz, 1H), 7.44 (d, J=8.4 Hz, 1H), 7.23 (d, J=8.8 Hz, 1H), 6.52 (d, J=10 Hz, 1H), 3.81 (s, 3H).

2,7-Dichloro-8-methoxyquinoline (5b)

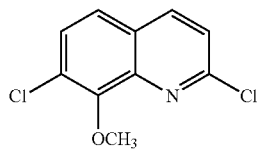

7-Chloro-8-methoxy-2-quinolinol (4b) (2.85 g, 13.6 mmol) was mixed with POCl$_3$ (6 mL) and allowed to reflux for 1.5 hours. To the concentrated contents, H₂O and AcOEt were added followed by NaHCO₃ to neutralize the mixture. The water layer was extracted with AcOEt, washed with saturated NaCl and dried with MgSO₄. The product was filtered through silica gel using CHCl₃ and recrystalized from CHCl₃-hexanes to afford the desired product as off white crystals (2.53 g, 82% yield): mp 103-104 □C; ¹H NMR (400 MHz, CDCl₃) 8.07 (d, J=8.0 Hz, 1H), 7.54 (d, J=8.8 Hz, 1H), 7.50 (d, J=8.0 Hz, 1H), 7.39 (d, J=8.8 Hz, 1H), 4.19 (s, 3H).

2-(4-(7-Chloro-8-methoxyquinolin-2-yloxy)phenoxy)propanoic acid (SH140)

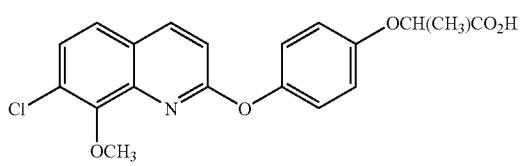

A mixture of 2,7-dichloro-8-methoxyquinoline (5b) (0.81 g, 3.6 mmol), 2-(4-hydroxyphenoxy)propionic acid (6) (0.65 g, 3.6 mmol), K2CO3 (1.23 g, 8.9 mmol) and DMF (10 mL) were heated overnight at 125° C. in an oil bath. The DMF was concentrated and water was added before it was filtered. The solution was chilled and 1 M HCl was added to pH 3. The water solution was extracted with AcOEt. The organic layer was washed with saturated NaCl and dried with MgSO₄. The product was chromatographed with 1:1 1:2 AcOEt-hexanes and recrystalized from CHCl₃-hexanes to afford the pure product as white crystals (0.50 g, 38% yield): mp 168-169° C.; ¹H NMR (400 MHz, CDCl₃) 8.06 (d, J=8.8 Hz, 1H), 7.40 (d, J=8.8 Hz, 1H), 7.36 (d, J=8.8 Hz, 1H), 7.20-7.14 (m, 2H), 7.06 (d, J=8.8 Hz, 1H), 7.00-6.94 (m, 2H), 4.83 (q, J=6.8 Hz, 1H), 3.88 (s, 1H), 1.71 (d, J=6.8 Hz, 3H). ¹³C NMR (100 MHz, CDCl₃) 177.5, 162.0, 154.6, 150.8, 148.2, 141.1, 140.3, 127.6, 126.5, 125.9, 123.3, 122.9, 116.3, 112.7, 73.0, 62.0, 18.7. IR (KBr) 3440 (OH), 1745 (C=O), 1615, 1490, 1465, 1425, 1330, 1260, 1235, 1200, 1145, 1130, 1085, 1045, 1010, 975, 950, 880, 860, 835, 795, 725, 615, 535 cm−1. ESI-MS m/z 374 (M+1)+. Anal. calc for C₁₉H₁₆NClO₅: C, 61.05; H, 4.31; N, 3.75. Found: C, 61.30; H, 4.19; N, 3.87. (R)-(+) enantiomer: mp 143-144° C.; [ ]D=29.4° (c=0.50, 0.1 M NaOH). Chiral HPLC separation ((S) enantiomer, 6.9 min, (R) enantiomer, 7.9 min) using Astec Chirobiotic T, 250 4.6 mm, 100 CH3OH: 0.1 AcOH: 0.1 TEA at 0.5 mL/min with detection at 243 nm.

(E)-N-(3-Bromo-2-methoxyphenyl)-3-ethoxyacrylamide (3c)

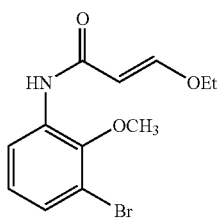

A mixture of 3-bromo-o-anisidine (2c) (4.50 g, 22.3 mmoles) and pyridine (15 mL) was placed in an icebath. (E)-3-ethoxy-2-propenoyl chloride (1) (3.75 g, 27.9 mmol) was added dropwise as the solution stirred continuously for one hour. The mixture was concentrated to remove the pyridine and was transferred to a seperatory funnel where AcOEt and water were added. Concentrated HCl was added until the aqueous layer was pH 1. The water layer was extracted twice with AcOEt and the organic layers were washed with saturated NaCl (25 mL) containing 1 M HCl (2 mL). The procedure was followed by a second wash of saturated NaCl (25 mL) containing saturated NaHCO₃ (5 mL). The organic layer was finally washed with saturated NaCl (25 mL). The product layer was dried and filtered through silica gel (2) using a solvent system of 1:1 followed by 2:1 hexanes-AcOEt. The product was chromatographed (2:1 1:1 hexanes:AcOEt) and recrystalized from 10:1 hexanes-AcOEt to afford light brown-orange crystals (3.35 g, 50% yield): mp 102-104 □C; ¹H NMR (400 MHz, CDCl₃) 8.35 (dd, J=8.4, 1.6 Hz, 1H), 7.65 (d, J=12.4 Hz, 1H), 7.52 (bs, 1H), 7.21 (dd, J=8.4, 1.6 Hz, 1H), 6.98 (t, J=8.4 Hz, 1H), 5.36 (d, J=12.0 Hz, 1H), 3.97 (q, J=7.2 Hz, 2H), 3.86 (s, 3H), 1.37 (t, J=7.2 Hz, 3H).

7-Bromo-8-methoxyquinolin-2-ol (4c)

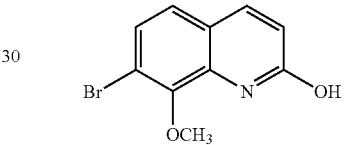

To stirred concentrated H₂SO₄ (30 mL), (E)-(N)-(3-bromo-2-methoxyphenyl)-3-ethoxypropenamide (3c) (2.11 g, 7.03 mmol) was added and allowed to stir overnight at room temperature. The solution was poured over ice and the resulting solid was filtered off, washed and dried. The desired product was obtained as a yellow solid (1.75 g, 98% yield): ¹H NMR (400 MHz, DMSO-d6) 11.44 (bs, 1H), 7.89 (d, J=9.2 Hz, 1H), 7.37 (s, 2H), 6.53 (d, J=8.8 Hz, 1H), 3.79 (s, 3H).

7-Bromo-2-chloro-8-methoxyquinoline (5c)

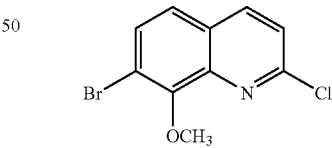

A mixture of 7-bromo-8-methoxy-2-quinolinol (4c) (2.22 g, 8.7 mmol) and POCl₃ (7 mL) was heated under reflux for 1.5 hours. After neutralization with NaHCO₃ and extraction with AcOEt, the residue was dissolved in CHCl₃ and filtered through silica gel to remove the brown polar impurities. The product (1.99 g, 84% yield) was obtained as white crystals upon recrystalization from AcOEt-Hexanes. mp 130-132° C.; ¹H NMR (400 MHz, CDCl₃), 8.06 (d, J=8.8 Hz, 1H), 7.66 (d, J=9.2 Hz, 1H), 7.42 (d, J=9.2 Hz, 1H), 7.39 (d, J=8.8 Hz, 1H), 4.17 (s, 3H).

2-(4-(7-Bromo-8-methoxyquinolin-2-yloxy)phenoxy)propanoic acid (SH135)

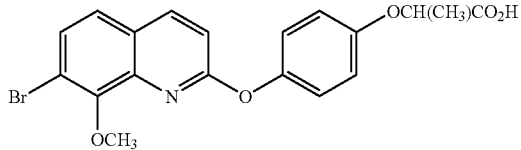

A mixture of 7-bromo-2-chloro-8-methoxyquinoline (5c) (0.54 g, 2.0 mmol), 2-(4-hydroxyphenoxy) propionic acid (6c) (0.36 g, 2.0 mmol), $K_2CO_3$ (0.69 g, 5.0 mmol) and DMF (5 mL) was heated at 125° C. for 8 hours. The solution was concentrated, dissolved in $H_2O$, filtered through Celite and chilled. The filtrate was acidified with 1 M HCl to pH 3. Extraction was performed with AcOEt and washed with saturated NaCl. The product was dried with $MgSO_4$, filtered through silica gel, purified by Column Chromatography (1:1 hexanes-AcOEt) and recrystalized from EtOH-hexanes to afford white crystals (0.43 g, 52% yield): mp 157-158° C.; $^1$H NMR (400 MHz DMSO-d6), 13.02 (bs, 1H), 8.39 (d, J=8.8 Hz, 1H), 7.59 (s, 2H), 7.28 (d, J=9.2 Hz, 1H), 7.21-7.16 (m, 2H), 6.97-6.91 (m, 2H), 4.84 (q, J=6.8 Hz, 1H), 3.73 (s, 3H), 1.51 (d, J=6.4 Hz, 3H). 1H NMR (400 MHz, CDCl3) 10.75 (bs, 1H), 8.05 (d, J=9.2 Hz, 1H), 7.49 (d, J=8.8 Hz, 1H), 7.32 (d, J=8 Hz, 1H), 7.17-7.15 (m, 2H), 7.07 (d, J=8.8 Hz, 1H), 6.99-6.93 (m, 2H), 4.82 (q, J=6.4 Hz, 1H), 3.86 (s, 3H), 1.70 (d, J=6.4 Hz, 3H). 13C NMR (100 MHz, DMSO-d6) 173.8, 162.0, 155.3, 151.8, 147.4, 141.5, 140.7, 126.9, 124.5, 123.5, 116.2, 113.7, 72.6, 62.0, 19.0. IR (KBr) 3430 (OH), 1715 (C=O), 1610, 1570, 1510, 1490, 1470, 1420, 1370, 1330, 1260, 1235, 1195, 1140, 1105, 1075, 1055, 1015, 995, 970, 885, 830, 785, 720, 625, 605, 525, 480 cm−1. MS (EI) m/z (%) 417 (M+, 99) 388 (25), 372 (20), 358 (45), 342 (66), 328 (32), 315 (26), 301 (13), 266 (13), 252 (19), 234 (6), 223 (16), 208 (27), 178 (48), 157 (44), 144 (13), 127 (93), 121 (18), 114 (60), 109 (12), 102 (25), 94 (15), 88 (17), 81 (12), 76 (28), 63 (40), 55 (17), 51 (21). HRMS (EI): m/z 419.0189 (M+, calcd. for $C_{19}H_{16}NO_5Br$, 419.0191). Anal. calcd. for $C_{19}H_{16}NO_5Br$: C, 54.56; H, 3.86; N, 3.35. Found: C, 54.76; H, 3.95; N, 3.25. R-(+) enantiomer: mp 150-151° C.; [ ]D=35.0° (c=0.50, 0.1 M NaOH). Chiral HPLC separation ((S) enantiomer, 6.2 min, (R) enantiomer, 7.4 min) using Astec Chirobiotic T, 250 4.6 mm, 100 $CH_3OH$: 0.1 AcOH: 0.1 $Et_3N$ at 0.5 mL/min with detection at 244 nm.

Exp 2877A
Evaluation of SH80(R), SH135(R), SH140(R) & SH144(R) Against Early Stage Mammary Adenocarcinoma 16/C in $C_3H$ Female Mice

| Cg | Treatment | Drug Route | Schedule | Total Dosage mg/kg | Mean Body Wt. Loss in g/mouse | Percent Body Wt. Loss | Day of Wt. Loss Nadir | Drug Death (day of death) | Median Tumor Burden in mg on d10 (range) |
|---|---|---|---|---|---|---|---|---|---|
| 1 | No Rx | — | — | — | +1.6 | +7.1 | 8 | — | 1143 (713-2207) |
| 2 | SH80R | IV | Q2dx7 | 420 | −0.8 | −3.4 | 2 | 0/5 | 0 (0-63) |
| 3 | SH80R | IV | Q2dx7 | 266 | −0.8 | −3.6 | 2 | 0/5 | 126 (0-320) |
| 4 | SH135R | IV | Q2dx7 | 378 | −2.4 | −10.5 | 12 | 0/5 | 0 (all zeros) |
| 5 | SH135R | IV | Q2dx7 | 238 | −0.8 | −3.6 | 2 | 0/4 | 63 (0-126) |
| 6 | SH140R | IV | Q2dx7 | 372 | −1.2 | −5.3 | 14 | 0/5 | 0 (0-63) |
| 7 | SH140R | IV | Q2dx7 | 234 | −1.2 | −5.5 | 2 | 0/5 | 63 (0-138) |
| 8 | SH144R | IV | Qd1, 3, 5 7-13 | 822 | −3.6 | −15.8 | 17 | 0/4 | 0 (0-88) |
| 9 | SH144R | IV | Qd1, 3, 5 7-13 | 513 | −1.2 | −5.3 | 2 | 0/5 | 320 (63-564) |

| Cg | T/C % | Tumor Free on d43 | Time to 1000 mg in days (range) | T − C (days) | Log Cell Kill Gross/Net | | Comments |
|---|---|---|---|---|---|---|---|
| 1 | — | 0/5 | 9 (8-11) | — | — | — | — |
| 2 | 0 | 0/5 | 25 (22-25) | 16 | 4.8 | 1.2 | Highly Active (++++) |
| 3 | 11 | 0/5 | 16 (13.5-31) | 7 | 2.1 | −1.5 | Active (+++) |
| 4 | 0 | 0/5 | 25.5 (23-30) | 16.5 | 5.0 | 1.4 | Highly Active (++++) |
| 5 | 5.5 | 0/4 | 23 (18-34) | 14 | 4.2 | 0.6 | Highly Active (++++) |
| 6 | 0 | 0/5 | 25 (23-26) | 16 | 4.8 | 1.2 | Highly Active (++++) |
| 7 | 5.5 | 0/5 | 21 (21-24) | 12 | 3.6 | 0 | Highly Active (++++) |
| 8 | 0 | 0/4 | 22.5 (18.5-36) | 13.5 | 4.1 | 0.5 | Highly Active (++++) |

-continued

Exp 2877A
Evaluation of SH80(R), SH135(R), SH140(R) & SH144(R) Against Early Stage
Mammary Adenocarcinoma 16/C in C₃H Female Mice

| 9 | 28 | 0/5 | 16 (11.5-18) | 7 | 2.1 | −1.5 | Active (+++) |
|---|----|-----|--------------|---|-----|------|--------------|

Mice: $C_3H$ females
Source: CRL-Raleigh
DOB: 4 Apr 05
DOA: 10 May 05
Ave. Wt. = 22 g/mouse
Tumor: Mam/16/C/RP/94
DOT: 31 May 05
Td = 1.0 day Preparation
  SH80(R), SH135 (R), SH140(R), SH144(R): All test agents were prepared in the same manner as detailed below:
Source: Hazeldine/Horwitz (KCl): white solid+3% EtOH+ 1% POE+0.5% $NaHCO_3$ (by volume)+$dH_2O$→solution (pH=9.0→7.0 with 1.0N HCl); 0.2 ml/mouse/IV injection.

Comments
Control: Cage 1—Tumor growth as expected; Tumor volume doubling time (Td)=1.0 day.
SH 80(R): Cage 2 was injected Q2dx7 starting day 1 at 60 mg/kg for a total dose of 420 mg/kg. This dose was well tolerated, producing a modest −3.4% weight loss (nadir day 2; full recovery day 15). Although the host recovery time was prolonged at 13 days, mice were in excellent condition for the entire duration of the trial, and overall weight loss was very modest, hovering between −1.7 to −3.4% (less than 1 gm) during the recovery period. SH80 (R) on this schedule was highly active, as expected, producing a 0% T/C and a 4.8 gross log kill (GLK); ++++ Activity rating.
  Cage3 was injected Q2dx7 starting day 1 at 38 mg/kg for a total dose of 266 mg/kg. There was a −3.5% weight loss sustained (nadir day 2; full recovery day 7). This dose was also active, producing an 11% T/C and a 2.1 (+++ Activity rating).
SH 135(R): Cage 4 was injected Q2dx7 starting day 1 at 54 mg/kg for a total dose of 378 mg/kg. There was a −10.5% weight loss sustained (nadir day 12; full recovery: day 20), indicative of adequate treatment. This dose was highly active, producing a 0% T/C and a 5.0 GLK (++++ Activity rating), slightly better than SH80(R).
  Cage 5 was injected Q2dx7 starting day 1 at 34 mg/kg for a total dose of 238 mg/kg. There was a −3.6% weight loss sustained (nadir day 2; full recovery: day 7). This dose was highly active, producing a 0% T/C and a 4.2 GLK (++++ Activity rating).
SH 140(R): Cage 6 was injected Q2dx7 starting day 1 at 48 mg/kg (with escalations of 54 mg/kg on days 7 & 9, and 60 mg/kg on days 11 & 13) for a total dose of 372 mg/kg. There was a −5.3% weight loss sustained (nadir day 14; full recovery: day 19). This dose was highly active, producing a 0% T/C and a 4.8 GLK (++++ Activity rating), essentially equivalent to SH80(R).
  Cage 7 was injected Q2dx7 starting day 1 at 30 mg/kg (with escalations of 34 mg/kg on days 7 & 9 and 38 mg/kg on days 11 & 13) for a total dose of 234 mg/kg. There was a −5.5% weight loss sustained (nadir day 2; full recovery: day 6). This dose was highly active, producing a 5.5% T/C and a 3.6 GLK (++++ Activity rating).
SH 144(R): Cage 8 was injected Q2dx3 starting day 1 at 57 mg/kg, then dosages were escalated and injections given daily from day 7 (63 mg/kg) to day 13 (125 mg/kg) for a total dose of 822 mg/kg. There was a −15.7% weight loss sustained (nadir day 17; full recovery day 19), indicative of a near lethal dose level. There were no drug deaths as mice recovered rapidly with a 2-day host recovery time. This dose was highly active, producing a 0% T/C and a 4.1 GLK (++++ Activity rating), inferior to SH80(R), SH135(R) and SH140(R).
  Cage 9 was injected Q2dx3 starting day 1 at 36 mg/kg, then dosages were escalated and injections given daily from day 7 (39 mg/kg) to day 13 (75 mg/kg) for a total dose of 513 mg/kg. There was a −5.3% weight loss sustained (nadir day 2; full recovery: day: 7). This dose was also active, producing a 28% T/C and a 2.1 GLK (+++ Activity rating).

Summary
  Three halo-methoxy quinoline compounds were evaluated for antitumor activity in comparison with SH80 against early stage mouse Mam 16/C in this trial. The Bromo-methoxy analogue [SH135(R)] was the most active, producing a 5.0 GLK at a total dose of 378 mg/kg, followed by the Chloromethoxy [SH140(R): 4.8 GLK at a total dose of 372 mg/kg]. SH80(R) produced a similar 4.8 GLK at a modestly higher total dose of 420 mg/kg. Least active in the series was the Fluoro-methoxy compound [SH144(R): 4.1 GLK at a total dose of 822 mg/kg]. Toxicity was not reached in this test with any of the compounds, though a −15.8% wt. loss was sustained by mice treated with the Fluoro analogue, indicating a near lethal dose level was delivered in this case. In general, weight loss nadir was greater and occurred later for the halo-methoxy compounds (Bromo: −10.5%; day 12; Chloro: −5.3%; day 14; Fluoro: −15.8%; day 17) than for SH80: flat −2.0 to 3.0% wt loss; days 2-15), perhaps indicating a potential for delayed toxicity with these compounds, or possibly a longer half-life. Interestingly, the Bromo and Chloro-methoxy analogues also were more active at the lower dose (displaying greater depth of activity) than SH80. Comparing lower doses, in order of highest log kill: SH135(R) (Cg 5: bromomethoxy): 4.2 log kill @ 238 mg/kg was superior to SH140R (Cg 7: chloro methoxy): 3.6 log kill @ 234 mg/kg; SH80(R) (Cg 3): 2.1 log kill @ 266 mg/kg; and SH144(R) (Cg 9: fluoro-methoxy): 2.1 log kill @ 513mg/kg.
  Compound ranking in this test from most to least active: bromo-methoxy SH135(R)>bromo SH80(R)=chloro-methoxy SH140(R)>fluoro-methoxy SH144(R).
  The high dose requirement (nearly as high as SH80, at least in this one test) could be viewed as a negative or no improvement over SH80. However, the retention of high activity (>3 log kill) for the lower doses of the Bromo-methoxy and Chloro-methoxy analogues would seem to be an indication of superiority and should be followed up with at least one more test in another tumor with three or four dose levels if possible.

EXAMPLE 3

The following illustrates representative pharmaceutical dosage forms, containing a compound of formula I ('Compound X'), for therapeutic or prophylactic use in humans.

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 01N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

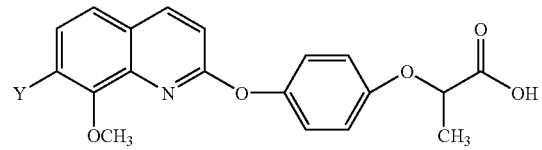

wherein Y is F or Br;
or a pharmaceutically acceptable salt thereof.

2. The compound of claim 1, wherein Y is F.

3. The compound of claim 1, wherein Y is Br.

4. The compound of claim 1, wherein the carbon bearing the methyl group is in the (R) configuration.

5. The compound of claim 1, wherein the carbon bearing the methyl group is in the (S) configuration.

6. A compound of claim 1 which is 2-(4-(7-fluoro-8-methoxyquinolin-2-yloxy)phenoxy)propanoic acid.

7. A compound of claim 1 which is 2-(4-(7-bromo-8-methoxyquinolin-2-yloxy)phenoxy)propanoic acid.

8. A composition comprising a compound of claim 1, in combination with a pharmaceutically acceptable diluent or carrier.

9. The composition of claim 8 wherein the composition is formulated for oral, parenteral, intravenous, intramuscular, subcutaneous, or topical administration.

10. The composition of claim 9 wherein the composition is formulated for oral administration and is in the form of a tablet, buccal tablet, troche, capsule, elixir, suspension, syrup, or wafer.

11. The composition of claim 10 wherein the composition comprises at least 0.1 weight % of the compound of formula I.

12. The composition of claim 11 wherein the composition comprises between about 2 weight % to about 60 weight % of the compound of formula I.

13. The composition of claim 8 wherein the composition is formulated for administration by infusion or injection, and the pharmaceutically acceptable diluent or carrier comprises water.

14. The composition of claim 13 wherein the composition comprises at least 0.1 weight % of the compound of formula I.

15. The composition of claim 14 wherein the composition comprises between about 2 weight % to about 60 weight % of the compound of formula I.

16. The composition of claim 13 wherein the compound of formula I is encapsulated in a liposome.

* * * * *

UNITED STATES PATENT AND TRADEMARK OFFICE
CERTIFICATE OF CORRECTION

PATENT NO. : 7,470,788 B2  
APPLICATION NO. : 11/223806  
DATED : December 30, 2008  
INVENTOR(S) : Horwitz et al.

Page 1 of 1

It is certified that error appears in the above-identified patent and that said Letters Patent is hereby corrected as shown below:

In the Specification

In Column 1, Lines 11-16, delete "The invention described herein was made in part with government support under NCI-NIH Grant Number CA82341 awarded by the National Cancer Institute. The United States Government has certain rights in the invention." and insert --This invention was made with government support under contract CA082341 awarded by the National Institutes of Health. The government has certain rights in the invention.-- therefor Signed and Sealed this
Fourteenth Day of April, 2020

Andrei Iancu
*Director of the United States Patent and Trademark Office*